US00PP13911P39

(12) United States Plant Patent
Gradziel et al.

(10) Patent No.: US PP13,911 P3
(45) Date of Patent: Jun. 24, 2003

(54) CLINGSTONE PEACH TREE NAMED 'GOODWIN'

(75) Inventors: Thomas M. Gradziel, Davis, CA (US); Mary Ann Thorpe, Davis, CA (US); James A. Beutel, Winters, CA (US); Robert E. Fenton, deceased, late of Port Hueneme, CA (US), by Susan D. Fenton, legal representative; Vilmos Beres, deceased, late of Guernesville, CA (US), by Marta M. Beres, legal representative; James F. Doyle, Clovis, CA (US)

(73) Assignee: The Regents of the University of California, Oakland, CA (US)

( * ) Notice: Subject to any disclaimer, the term of this patent is extended or adjusted under 35 U.S.C. 154(b) by 3 days.

(21) Appl. No.: 09/891,285

(22) Filed: Jun. 27, 2001

(65) Prior Publication Data

US 2003/0009796 P1 Jan. 9, 2003

(51) Int. Cl.[7] ..... A01H 5/00

(52) U.S. Cl. ..... Plt./190

(58) Field of Search ..... Plt./190

*Primary Examiner*—Bruce R. Campell
*Assistant Examiner*—Anne Marie Grünberg
(74) *Attorney, Agent, or Firm*—Burns, Doane, Swecker & Mathis, L.L.P.

(57) ABSTRACT

A new and distinct cultivar of early-season clingstone peach tree (i.e., *Prunus persica*) is provided. Attractive fruit is formed that is well suited for processing having uniform yellow flesh that is free from red staining at the pit cavity. The fruit color, flavor, and texture are believed to be superior to the 'Dixon' and 'Andross' cultivars (both non-patented in the United States). The fruit ripens at approximately four days earlier than the 'Andross' cultivar. The pink flowers are medium-sized and non-showy and the growth habit is upright-spreading.

2 Drawing Sheets

BOTANICAL/COMMERCIAL CLASSIFICATION

*Prunus persica*/Clingstone Peach Tree.

VARIETAL DENOMINATION cv. 'Goodwin'.

BACKGROUND OF THE INVENTION

The new clingstone peach cultivar was created at Davis, Calif., U.S.A., in 1983 as part of a breeding program of the University of California for the development of improved processing peaches. During the course of the breeding program that yielded the new cultivar of the present invention, many seedlings were developed and evaluated. An objective of the program was to develop a superior replacement cultivar for the early-maturity 'Dixon' and 'Andross' cultivars (both non-patented in the United States). The 'Dixon' cultivar originated at Linden, Calif., U.S.A., and was introduced during 1956. Trees of this cultivar are recognized to be highly productive and yield yellow-gold fruit that commonly displays a pink to red coloration at the pit area that is attributable to the formation of anthocyanins. The red coloration often oxidizes to brown when canned and thereby provides less than optimum fruit color as well as an undesirable brown staining of the canned syrup. Additionally, the red-stained stone or endocarp of the 'Dixon' cultivar tends to be prone to breakage during processing and sometimes imparts unwanted pit fragments to the fruit flesh that are difficult to remove.

The 'Andross' cultivar originated at the University of California at Davis, Calif., U.S.A., and was introduced in 1964. Trees of the 'Andross' cultivar consistently set heavy crops, have leaves with globose glands, and flowers of the large non-showy type. The 'Andross' cultivar also produces fruit having red-staining of the pit area and unwanted higher frequencies of stone or endocarp fragments in the processed fruit flesh.

The female parent (i.e., seed parent) of the new cultivar was a University of California processing peach breeding line named '11, 11-37' (non-patented in the United States). The male parent (i.e., pollen parent) of the new cultivar was the 'Dr. Davis' cultivar (non-patented in the United States). The parentage of the new cultivar of the present invention can be summarized as follows:

'11, 11-37'×'Dr. Davis'.

Four seedlings from this cross were recovered in 1984, and have been carefully studied and evaluated thereafter. The new cultivar was selected from among these and was designated 'R, 7-5' and 'Early #3'.

It was found that the new clingstone peach cultivar of the present invention:

(a) Exhibits an upright-spreading growth habit,
(b) Forms medium-sized non-showy pink flowers,
(c) Forms attractive fruit having uniform yellow flesh that is free from red staining at the pit cavity,
(d) Ripens approximately four days earlier than the 'Andross' cultivar (non-patented in the United States), and
(e) Is particularly well suited for processing.

The new cultivar of the present invention can be readily distinguished from its '11, 11-37' and 'Dr. Davis' parental cultivars. More specifically, the '11, 11-37' and 'Dr. Davis' cultivars commonly ripen at approximately the same time and approximately 10 to 14 days after the new cultivar of the present invention. Also, the fruit of the new cultivar commonly displays a slightly asymmetrical shape with a noticeable bulging at the suture area. In contrast, the fruit of the '11, 11-37' and 'Dr. Davis' cultivars is characteristically symmetrical in shape.

The new cultivar has been asexually propagated at Davis, Calif.; Winters, Calif.; and Parlier, Calif. U.S.A., by grafting on 'Nemared' peach rootstock (non-patented in the United States). Such propagation has confirmed that the characteristics of the new cultivar are stable and are reliably transmitted to subsequent generations.

The new cultivar of the present invention is considered to offer superior characteristics when compared to the previously-available early-maturity processing peach cultivars 'Dixon' and 'Andross'. Unlike these cultivars, the new cultivar is free from red staining at the pit cavity. The fruit flesh is bright yellow to yellow-gold and the fruit color, flavor and texture have been rated superior to the 'Dixon' and 'Andross' cultivars. The fruit skin is slightly less pubescent than that of the 'Andross' cultivar with a more uniform golden-yellow color. The pit size is medium to slightly below average. Some split pits occur during high crop years however at a lower rate than the 'Dixon' and 'Andross' cultivars. The crop yield for the new cultivar appears to average and somewhat lower than that of the 'Andross' cultivar thus commonly requiring less thinning following a high-chill winter. The fruit hangers are similar to those of the 'Andross' cultivar and a bit denser. The leaves are medium to dark green and similar in size to those of the 'Andross' cultivar. Unlike the 'Andross' cultivar, reniform leaf glands are present. The flowers of new cultivar are pink and non-showy.

The new cultivar of the present invention has been tested in plantings at Davis, Calif.; Winters, Calif.; and Parlier, Calif., U.S.A.

Wood of the new cultivar has been subjected to the virus indexing program of Foundation Plant Materials Service, University of California at Davis, Calif., U.S.A. All indices have proven to be negative for viruses for foundation trees of this genotype being maintained by such Foundation Plant Materials Service.

The new cultivar of the present invention has been named 'Goodwin'.

DETAILED DESCRIPTION OF THE PHOTOGRAPHS

The accompanying photographs show typical specimens of trees, foliage, fruit, and stone of the new cultivar of the present invention in color as true as it is reasonably possible to make the same in color illustrations of this character. Trees of the new cultivar were being grown on 'Nemared' peach rootstock at Davis, Calif., U.S.A.

DETAILED DESCRIPTION

Figure 1:
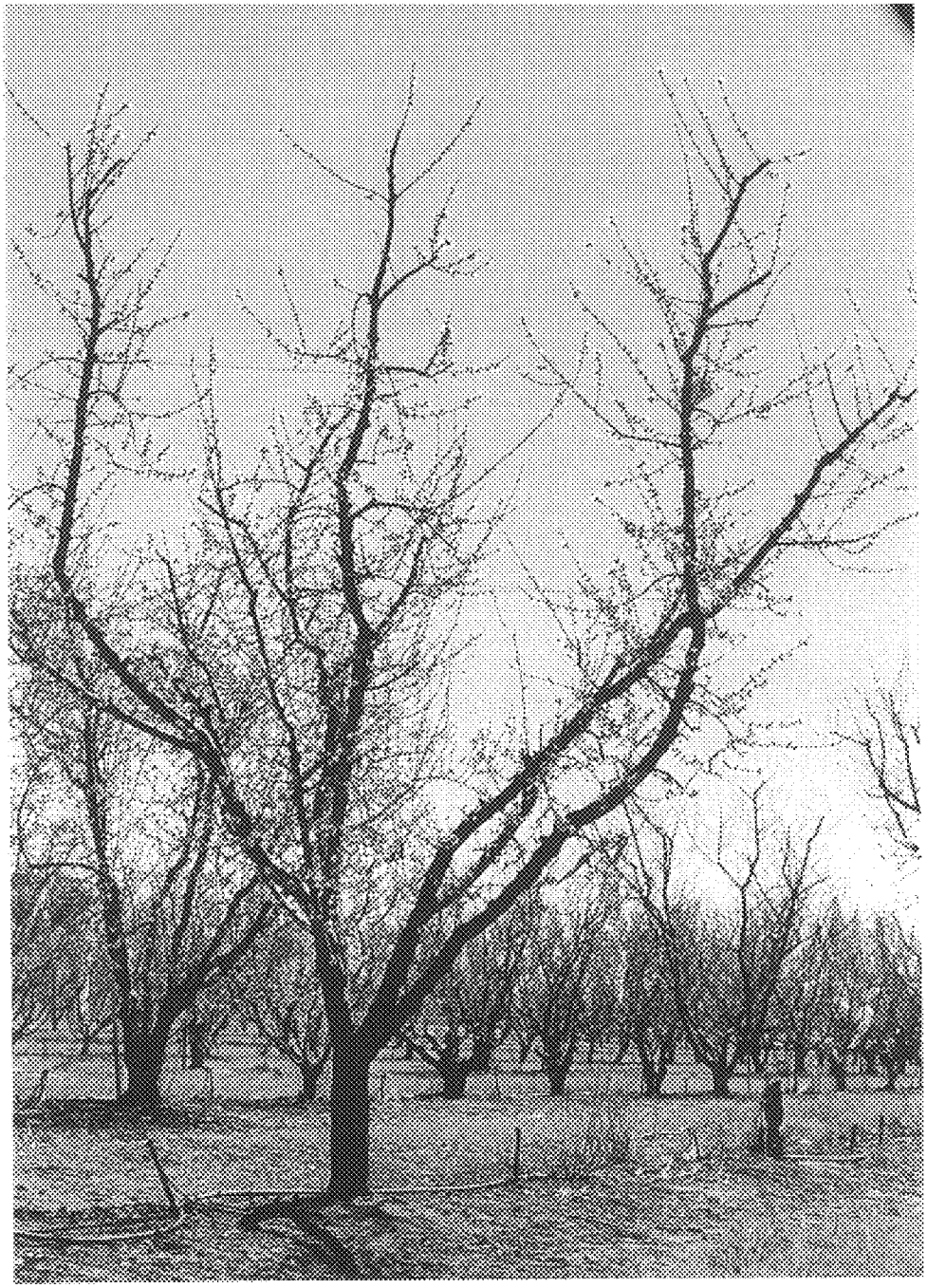
FIG. 1 illustrates trees having an age of approximately six years on Mar. 10, 2000. The non-showy flowers are shown as well as the upright-spreading growth habit.
Figure 2:
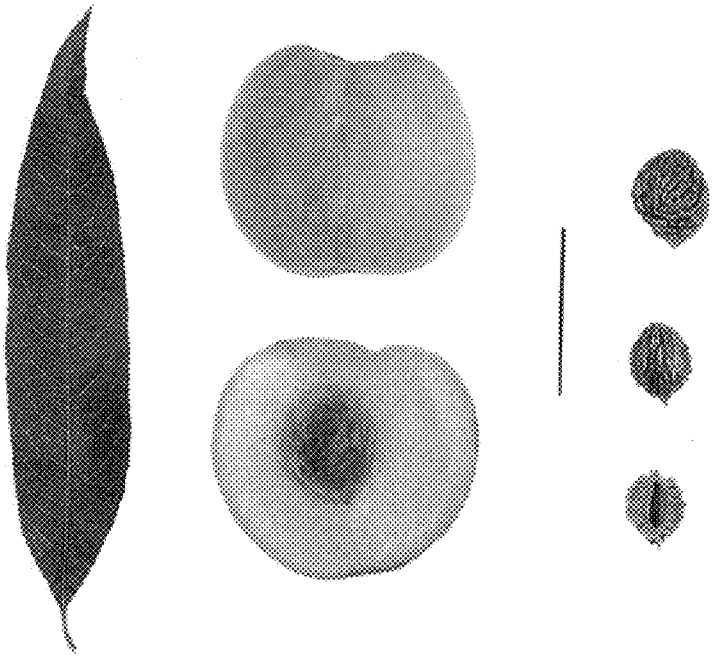
FIG. 2 illustrates on Aug. 3, 1999 external and internal views of the fruit, stone, and of a leaflet of the new cultivar.

The following is a detailed description of the new cultivar obtained from the observation of vegetatively propagated progeny of the new cultivar during the 1999 and 2000 growing seasons. The trees were grown on 'Nemared' peach rootstock at the Wolfskill Experimental Orchards of the University of California located at Winters, Calif., U.S.A., and at the University of California Pomology Research Plots located at Davis, Calif., U.S.A. Color designations are presented with reference to the "Dictionary of Color" by Maerz and Paul, First Edition (1930). More common color terms are to be accorded their customary dictionary significance.

Tree:

*Size.*—Medium. The trees resulting from the asexual propagation of 1998 during the fall of 2000 had a height of approximately 3.3 meters, a breadth of approximately 3.4 meters across the crown, and commonly possessed approximately four scaffolds.

*Vigor.*—Medium. Produced approximately 0.61 to 0.92 meter of new growth during the 2000 growing season.

*Growth.*—Upright-spreading.

*Hardiness.*—Hardy under typical Sacramento Valley climatic conditions.

*Production.*—Productive.

*Bearing.*—Regular bearer.

Trunk:

*Size.*—Medium to large. The trunk diameter at 10 cm above the ground is approximately 21 cm. The scaffold diameters at the base of the scaffolds are approximately 10 cm.

*Texture.*—Relatively coarse with substantial scarfskin.

*Color.*—The bark color ranges from brown-grey (15-H-7 Olive Brown) to more medium brown (8-H-10 Chocolate Brown).

*Lenticels.*—Numerous, medium in size, flattened and generally oval-shaped. Typically the lenticels range from approximately 2 to 6 mm in width at a right angle to the trunk and are approximately 1 to 2 mm in height. The lenticel surface is light brown in coloration (13-J-9 Hazel Brown).

Branches:

*Size.*—Medium.

*Texture.*—Medium.

*Color.*—Mature shoots are light brown (14-J-9 Mummy Brown) to darker brown (7-H-12 Mohawk Brown). The current season's shoots are pale light green (18-K-5). The exposed surfaces are commonly tinged rose-red (5-K-10 Ember). The coloration of the new expanding shoot tips is bright yellow green (17-L-4).

*Lenticels.*—At a right angle to the shoots, and light in coloration.

*Internode length.*—On current season's hanger shoots the length between nodes commonly is approximately 10 to 25 mm.

Leaves:

*Size.*—Medium to large. Typical length from vigorous current season's growth is approximately 16.1 to 19.6 cm including the petiole, and typical width is approximately 3.7 to 4.6 cm. The leaf thickness is average.

*Form.*—Lanceolate.

*Apex.*—Acuminate and often with a slight curve downward.

*Aspect.*—The blade commonly ranges from substantially flat to somewhat folded upwards.

*Color.*—The upper surface is dark green (23-J-5 Elm Green) and the lower surface is a much lighter grey-green (21-1-6). The primary and mid-vein on the under surface is pale yellow-green (17-H-1).

*Margin.*—Crenate and occasionally double crenate. The crenations are relatively large and uniform. The leaf margins commonly range from straight to moderately undulate.

*Petiole.*—Generally medium in size, commonly approximately 8 to 12 mm in length, approximately 2 mm in thickness, and pale yellow-green in coloration (17-K-3).

*Glands.*—Small to medium in size, almost always reniform, alternate, commonly 1 to 3 on the petiole, and frequently 0 to 3 additional glands can be observed at the base of the leaf blade. The coloration is shiny light green-yellow (17-K-6) and often with a reddish center.

*Stipules.*—Linear lanceolate in configuration, most are early deciduous, margins are serrate, commonly approximately 6 to 9 mm in length, and the coloration of young stipules commonly is light green-yellow (17-K-5) with darkening to brownish upon aging.

Fruit:

*Maturity when described.*—Full commercial maturity.

*Picking.*—First pick was Jul. 24, 2000 and last pick was Jul. 29, 2000.

*Season of maturity.*—Approximately four days earlier than the 'Andross' cultivar.

*Size.*—Uniform, large. Average axial diameter is approximately 60 to 65 mm, the average suture diameter is approximately 65 to 71 mm, and the average cheek diameter is approximately 64 to 70 mm.

*Form.*—In lateral aspect the fruit is slightly oblate, and in the apical aspect is nearly globose with slight variability. Most frequently the fruit is slightly asymmetrical.

*Suture.*—As an inconspicuous line. Is slightly deeper at the base and with a slight depression at the apex.

*Ventral surface.*—Relatively smooth and only occasionally lipped.

*Base.*—Rounded to slightly truncate in form. The base angle is slightly variable and most often is at a right angle to the fruit axes.

*Stem cavity.*—Broad and moderately deep, commonly approximately 3.3 cm in length on average, approximately 2.2 cm in width on average, and approximately 1.6 cm in depth on average.

*Apex.*—Commonly rounded with a low to medium tip. The pistil point commonly is apical.

*Pistil point.*—Most frequently is oblique.

*Stem length.*—Medium, and commonly averages 1.0 cm.

*Stem thickness.*—Commonly averages approximately 3 to 3.3 mm and usually is more thickened at the distal end.

*Skin pubescence.*—Fine, short, and matted. Commonly with slightly less pubescence than the 'Andross' cultivar.

*Skin tendency to split.*—None observed.

*Skin color.*—The primary ground color is uniform orange-yellow (10-J-6). The fruit surface has a moderate amount of blush coloration that commonly covers approximately 20 to 60 percent of the total surface. Fruit exposed to direct sunlight commonly possesses more blush. The blush pattern is primarily washed with a moderate amount of dark mottling.

The blush color ranges from dark garnet red (7-E-5) to a lighter shade of red (6-K-7) with a range of variation in between.

*Flesh color.*—A uniform yellow coloration from the skin to the stone cavity (10-K-5).

*Flesh texture.*—Firm, and non-melting.

*Flesh fibers.*—Few in number, short and fine.

*Ripening.*—Ripens evenly.

*Flavor.*—Excellent quality, rich and well-balanced. Rated superior to that of the 'Andross' cultivar in taste trials.

*Aroma.*—Pleasant and moderate.

*Eating quality.*—Good.

*Canning quality.*—Very good.

*Stone type.*—Clingstone with flesh connected over the entire stone surface.

*Stone size.*—Medium to slightly below average, and commonly averages approximately 28.6 mm in length, approximately 22.2 mm in width, and approximately 17.3 mm in thickness.

*Stone fibers.*—Numerous very short and fine fibers attached laterally to the stone.

*Stone form.*—Variable, but most often slightly obovate.

*Stone base.*—Typically positioned at right angles to slightly oblique to the stone axis.

*Stone hilum.*—Medium to small in size, well defined, and surrounded by a raised collar.

*Stone apex.*—Generally rounded with a broad rather blunt tip.

*Stone sides.*—Variable and most often nearly equal.

*Stone surface.*—Moderately coarse with the heaviest grooving being present apically over the lateral apical shoulders. Several deep grooves are present near the dorsal and ventral edges and meet the edges at an oblique angle.

*Ventral edge.*—Medium in width with several low wings.

*Dorsal edge.*—Somewhat variable in form, and most commonly the dorsal suture is moderately narrow with a deep groove extending from the base to the apical shoulder. The apical shoulder area is somewhat eroded and somewhat concave in configuration.

*Stone color.*—When dry, light clay-brown (13-B-8).

*Tendency to split.*—Low to moderate, and similar to that of the 'Andross' cultivar.

Flowers:

*Chilling season.*—Low to medium for the growing location. There were approximately 1,200 chilling hours below 45° F. for the 1999 winter season, and approximately 770 hours below 45° F. for the 2000 winter season.

*Buds.*—Medium in size, conic in form, plump, free of the stem with pubescent surfaces of light grey coloration. The exterior bud scale ranges from grey (15-A-6 Beaver Grey) to grey-brown (15-A-8 Winter Leaf Brown) in coloration. The buds are hardy under typical climatic conditions of the Sacramento Valley. There commonly are one to two floral buds per node and most frequently two floral buds per node.

*Bloom timing.*—Mid-season in relation to other commercial cling peach cultivars. During 1999 and 2000 the bloom periods were substantially the same as the 'Andross' cultivar.

*Size.*—The flower size is medium and non-showy. The fully expanded flower diameter commonly is approximately 26 to 32 mm.

*Bloom quality.*—Commonly abundant throughout the tree. There commonly are two flowers per node.

*Petals.*—The petal size is medium to large and commonly ranges from approximately 12 to 14 mm in length and from approximately 8 to 10 mm in width. The petal number is five. The petal form varies from broadly ovate to at times nearly oval. The petal color is very light pink (1-B-1) at the central area and dark pink (1-E-2) along the margin. The petal claw is relatively narrow and truncate in form. The claw color is dark pink (1-G-2). The petal margins are moderately undulate and the petals are substantially cupped inward. The petal apices are commonly rounded with no tip.

*Pedicel.*—Relatively short and commonly exhibits a length of approximately 1 to 1.5 mm and an average thickness of approximately 1 mm. The coloration is light green (18-I-7) and the surface is glabrous.

*Nectaries.*—Moderately bright orange (11-J-11) and become slightly darker at maturity.

*Calyx.*—Glabrous and quite rugose, and the coloration is light maroon (5-J-4) with areas of green (19-L-2 Jewel Green) especially basally, and darkening to intense maroon (6-J-5 Rubaiyat).

*Sepals.*—With greyish pubescence, average in size, conic in form, and dark maroon (6-J-4 to 6-J-5) in coloration.

*Anthers.*—Average in size, red dorsally (5-L-11 Brickdust) and tan ventrally (Chamois 11-I-5).

*Stamens.*—Medium in length and commonly slightly longer than the pistil at full maturity. The filament color is nearly white when the bloom first opens, and darkens to dull light violet (4-H-3) with senescence.

*Pollen.*—Abundant, bright yellow (Empire Yellow 9-K-3) in coloration.

*Pistil.*—Pubescent basally over the ovary, and less so near the stigma and over the upper style area. The length commonly is approximately 12 to 15 mm including the ovary. The coloration basally is pale green (17-J-3) and a paler green (17-J-1) over the upper style area.

Major use: Canning.

Keeping quality: Good. In cold storage tests where fruit was stored at 4° C. under ambient conditions with no controlled atmosphere for 10 days, fruit processing was carried out with no detectable loss in eating quality (i.e., flavor, color and firmness). Longer tests were not performed since 10 days is the maximum expected storage time for peach fruit of this maturity period. Previous tests had shown that the 'Dr. Davis' parental cultivar displays exceptional cold storage quality with no detectable loss of quality following in excess of 15 days in cold storage.

Resistance to diseases: Average. Diseases evaluated included brown rot disease (*Monilinia fructicola*) of the fruit, and powdery mildew (*Sphaerotheca pannosa*) and peach leaf-curl (*Taphrina deformans*) of the foliage. The brown-rot resistance was determined through controlled laboratory screenings. Conidal suspensions of *Monilinia fructicola* were produced by washing 5 to 7 day-old PDA cultures with 20 ml sterile distilled water containing 0.01% TWEEN 20 wetting agent. The inoculum was filtered through four layers of sterile cheesecloth to minimize the presence of mycelial fragments and was adjusted to a concentration of 2×104 conidia per ml. Ten microliters of conidial suspension were deposited on the fruit surface which was previously determined to be free of visible injury by examination with a stereo microscope. Inoculated fruit was incubated for 72 hours at 22 to 25° C. in the dark at approximately 95% relative humidity. Lesion diameters were recorded 72 hours after inoculation. Diameters on the 'Goodwin' fruit averaged 19 mm which was generally comparable to that formed on the 'Dr. Davis' fruit which averaged 22 mm. The 'Dr. Davis' parent is widely considered to have only average resistance to brown rot. The powdery mildew resistance was evaluated through the observation of natural field infections. It was rated during 1995 at Winters, Calif., in a field epiphytotic evaluation block. Numerical rating were based on leaf symptoms where "1"=no disease, and "6"=several disease. 'Goodwin' received a "1" rating as did the 'Dr. Davis' parent. For comparative purposes the 'Dixon' and 'Andross' cultivars were rated "3". The peach leaf-curl resistance also was evaluated through the observation of natural field infections. It was rated during 1995 at Winters, Calif., in a field epiphytotic evaluation block that experienced heavy rains and poor fungicide spray control. 'Goodwin' received a "4" rating, 'Dr. Davis' a "3" rating, and 'Dixon' and 'Andross' each received a "4" rating on the same scale identified above.

Resistance to insects: Average. The major insect pest to Peach trees is the twig-borer (*Anarsia lineatella*) which feeds on young peach tree shoots possibly causing their eventual collapse and on the ripening fruit resulting in worm feeding damage and greater susceptibility to fruit molding. The incidence of damage for 'Goodwin' from this insect was observed to be comparable to that of the 'Dr. Davis', 'Dixon' and 'Andross' cultivars.

We claim:

1. A new and distinct cultivar of clingstone peach tree having the following combination of characteristics:

(a) exhibits an upright-spreading growth habit,
(b) forms medium-sized non-showy pink flowers,
(c) forms attractive fruit having uniform yellow flesh that is free from red staining at the pit cavity,
(d) ripens approximately four days earlier than the 'Andross' cultivar (non-patented in the United States), and
(e) is particularly well suited for processing;

substantially as illustrated and described.

* * * * *